United States Patent [19]

Bergthaller et al.

[11] 4,355,185
[45] Oct. 19, 1982

[54] PROCESS FOR THE PREPARATION OF 2-MERCAPTOALKYL-SULPHIDES AND 2-MERCAPTOALKYLETHERS

[75] Inventors: Peter Bergthaller; Peter Wenzl, both of Cologne, Fed. Rep. of Germany

[73] Assignee: Agfa-Gevaert Aktiengesellschaft, Leverkusen, Fed. Rep. of Germany

[21] Appl. No.: 181,044

[22] Filed: Aug. 25, 1980

[30] Foreign Application Priority Data

Aug. 29, 1979 [DE] Fed. Rep. of Germany ....... 2934948

[51] Int. Cl.³ .......................................... C07C 148/00
[52] U.S. Cl. ......................................... 568/50; 568/39; 568/45; 568/57; 568/62
[58] Field of Search ....................... 568/39, 45, 57, 50, 568/62

[56] References Cited

U.S. PATENT DOCUMENTS 3,615,624 10/1971 Smith et al. .......................... 96/114
3,692,753 9/1972 Smith et al. .......................... 96/114
4,002,686 1/1977 Davis et al. ............................ 568/69

OTHER PUBLICATIONS

Cossar, et al., J. Org. Chem., vol. 27, pp. 93–95 (1962).

*Primary Examiner*—Robert Gerstl
*Assistant Examiner*—D. G. Rivers
*Attorney, Agent, or Firm*—Connolly and Hutz

[57] ABSTRACT

2-Mercaptoalkylsulphides and 2-mercaptoalkylethers are obtained by the hydrazinolysis of 3-thiaalkylisothiuronium salts and 3-oxaalkylisothiuronium salts.

6 Claims, No Drawings

PROCESS FOR THE PREPARATION OF 2-MERCAPTOALKYL-SULPHIDES AND 2-MERCAPTOALKYLETHERS

The invention relates to a process for the preparation of 2-mercaptoalkylsulphides, in particular 3-thiaalkane-1-thiols, and 2-mercaptoalkylethers.

2-Mercaptoalkylsulphides, in particular 3-thiaalkane-1-thiols, and 2-mercaptoalkylethers, are among those organic compounds which have a particularly unpleasant and persistent smell. They are to some extent high-boiling, partly undistillable and generally water-insoluble oils or waxes and, in spite of their unpleasant characteristics, they constitute valuable intermediate products for the synthesis of other organic sulphur compounds. They are particularly suitable as intermediate products for the synthesis of thioethers, thiolesters, sulphoxides and sulphones.

However, up till the present time, the extremely difficult methods for obtaining and processing 2-mercaptoalkylsulphides and 2-mercaptoalkylethers prevented their commercial use, especially as many of the compounds which are in principle available from these compounds could only be prepared in satisfactory yield and purity from pure starting materials.

According to the processes known hitherto, pure 2-mercaptoalkylsulphides and 2-mercaptoalkylethers could only be obtained by means of after-purification by distillation or, optionally, crystallisation. No process which produces directly pure 2-mercaptoalkylsulphides and 2-mercaptoalkylethers, in particular free of disulphide, is known. It is only possible to prepare and purify 2-mercaptoalkylsulphides in complex installations.

The most usual process for the preparation of 2-mercaptoalkylsulphides comprises reacting the corresponding 2-hydroxyalkylsulphide with thiourea in the presence of a strong acid, at a temperature of approximately 100° C., to produce isothiuronium salts which are then dissociated using excess aqueous alkali. This dissociation produces only moderate yields, and higher yields are only obtained when the thiol can be distilled off using steam. In many cases, the yields are unfavourable, which is unacceptable because of the increased cost for removing the waste liquors of the process which contain considerable quantities of sulphur. Processing is made even more difficult by the fact that the isothioureas, cyanamides and dicyandiamides, produced as by-products, rapidly form difficultly soluble sludges and smears under the conditions of the reaction, which sludges and smears entrain 2-mercaptoalkylsulphide and impede separation. This applies similarly to 2-mercaptoalkylethers which may be prepared from 2-halogen alkylethers.

An alternative process for the synthesis of 2-mercaptoalkylsulphides comprises reacting thiols with episulphides, as described by Fokin et al., Izv. Akad. Nauh. SSSR Ser. Khim (1975) 660–662. Non-uniform products are produced thereby due to the high polymerisation tendency of the episulphides and, moreover, the process cannot be carried out commercially due to the extreme toxicity of the episulphides, particularly the simplest substance of the series. 2-Mercaptoalkylethers cannot usually be prepared by means of episulphides.

This applies similarly to the reaction of 2-chloroalkylsulphides and 2-chloroalkylethers with thiol carboxylates or thio carbon dioxide derivatives, e.g. dialkyl dithio carbamates, in which intermediate products are produced which have to be separated from alkali. Also in these cases, the extremely high toxicity of 3-thiol alkyl chlorides ($\beta$-chloroalkylsulphides) means that commercial application is almost impossible.

In connection with the known preparation processes of 2-mercaptoalkylsulphides, reference is made to the corresponding chapter in Houben-Weyl, Methoden der organischen Chemie, Volume 9, pages 12–18, also pages 35–39, and also to the corresponding description in Weygand-Hilgetag "Organische chemische Experimentierkunst", 4th Edition, pages 654–655.

Many secondary products from 2-mercaptoalkylsulphides are of commercial interest. 1-amino-3,6-dithiaalkanes, obtainable according to the process described in German Offenlegungsschrift No. 1,904,149, are used for example as intermediate products for monomers which are used in photographic emulsion technology. For example, the N-3,6-dithiaalkyl acrylic amides described in German Offenlegungsschrift No. 1,904,147 give a protective colloidal effect towards silver halide crystals to the copolymer framework, into which they are built.

Thiaalkanes which can be prepared from 2-mercaptoalkylsulphides are extremely suitable as a dissolution and crystallisation medium for silver halide for the preparation of highly sensitive silver halide emulsions having a narrow particle-size distribution.

Also during the preparation of thia crown ethers from bis-(2-mercaptoalkyl)-ethers, these must be present in very high purity if the yield and purity of the thia crown ethers are to satisfy the requirements for photographic applications in particular.

Therefore, there is an interest in the process for the preparation of 2-mercaptoalkylsulphides and 2-mercaptoalkylethers in which these may be produced in very high purity and may also be further used directly, optionally without a purification step.

Surprisingly, it has been found that 2-mercaptoalkylsulphides and 2-mercaptoalkylethers are obtained to some extent in yields of more than 90% of the theoretical yield when 3-thiaalkylisothiuronium salts or 3-oxaalkylisothiuronium salts are subjected to hydrazinolysis. The reaction generally takes place at a temperature of from 0° to 120° C., preferably between 20° and 80° C., and at a pH value of from 6 to 12, preferably between 7 and 9. However, if necessary, the process may also be carried out outside these ranges.

It has been found in particular that compounds of the formula (I)

are obtained if isothiuronium salts of the formula (II)

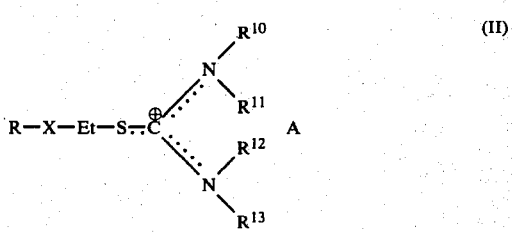

are reacted with hydrazines of the formula (III)

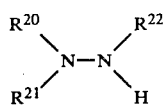

in which:
- R represents an organic radical, which may be substituted, in particular an alkyl, aryl or aralkyl radical which may be substituted, which radicals may be linked with each other and/or may be interrupted by at least one sulphur and/or oxygen atom;
- X represents an oxygen or sulphur atom;
- Et represents an ethylene group which may be substituted which may be part of a, preferably 5- or 6-membered ring;
- $R^{10}$, $R^{11}$, $R^{12}$, $R^{13}$ which may be the same or different, represent hydrogen; an alkyl group, preferably having from 1 to 6 carbon atoms which may be substituted; an aryl group, preferably a phenyl group, which may be substituted and/or at least one pair from the group of substituents $R^{10}$ to $R^{13}$ represents the atoms required to complete a preferably 5- or 6-membered, preferably heterocyclic ring, in particular, $R^{10}$ and $R^{11}$ may together represent $-(CH_2)_4-$; $-(CH_2)_5-$ and $-C_2H_4-O-C_2H_4-$ or $R^{10}$ and $R^{12}$ may together represent an alkylene group having from 2 to 4 carbon atoms;
- $R^{20}$, $R^{21}$, $R^{22}$ which may be the same or different, represent hydrogen; an alkyl group, preferably having from 1 to 5 carbon atoms which may be substituted; an aryl group which may be substituted and/or $R^{20}$ together with $R^{21}$ may represent the atoms required to complete a preferably 5- or 6-membered ring;
- represents an anion, which may be multivalent, preferably a chloride or sulphate ion.

In a particularly preferred embodiment of the invention, the compounds according to formula (I) correspond to a structure according to formula (Ia) or (Ib):

$$R^1 \!\!-\!\!\left[\!(X\!-\!\underset{\underset{R^2}{|}}{\overset{\overset{R^3}{|}}{C}}\!-\!\underset{\underset{R^5}{|}}{\overset{\overset{R^4}{|}}{C}})_m\!SH\right]_n \quad (Ia)$$

$$R^6 \!\!-\!\!\left[\!O\!-\!(\underset{\underset{R^2}{|}}{\overset{\overset{R^3}{|}}{C}}\!-\!\underset{\underset{CH_2\!-\!SH}{|}}{\overset{\overset{R^4}{|}}{C}}\!-\!O)_p\!B\right]_o \quad (Ib)$$

in which:
- $R^1$ represents an n-valent organic radical, particularly:
  1. an aliphatic radical, which may be substituted by aryl or interrupted by arylene, particularly phenylene, or by O or S atoms, preferably having from 2 to 20 carbon atoms,
  2. an alicyclic radical, preferably having from 5 to 7 carbon atoms,
  3. an aryl radical, which may be substituted, preferably phenyl, chlorophenyl or o-carboxy phenyl,
  4. an aralkyl group, which may be substituted preferably benzyl,
- $R^2$, $R^3$, $R^4$ and $R^5$ which may be the same or different represent hydrogen; an alkyl group, preferably having from 1 to 6 carbon atoms which may be substituted; an aryl group, which may be substituted, preferably phenyl, and/or at least one pair from the group $R^2$ to $R^5$ represents the atoms required to complete a preferably 5- or 6-membered ring;
- X represents an oxygen atom or a sulphur atom;
- $R^6$ represents H or an o-valent organic radical, preferably:
  1. an aliphatic radical, which may be substituted by aryl or cycloalkyl or interrupted by arylene, particularly by phenylene, preferably having from 2 to 10 aliphatically bound carbon atoms,
  2. a radical derived from a polyalkylene oxide, interrupted by ether groups, preferably having from 4 to 20 carbon atoms,
  3. an aromatic radical, preferably phenyl or phenylene, which radical may be interrupted by alkylene groups,
  4. an alicyclic radical, preferably having from 5 to 7 carbon atoms,
  5. an aralkyl radical, which may be substituted preferably benzyl or phenethyl;
- $R^6$ may be interrupted by at least one oxygen and/or sulphur atom,
- m represents an integer, preferably from 1 to 100;
- n represents an integer, preferably from 1 to 4;
- o represents an integer, preferably from 1 to 3;
- p represents an integer greater than 1, preferably from 2 to 20;
- B represents H or $-CO-R^8$; and
- $R^8$ represents $-NH-$alkyl; $-NH-$aryl; $-O-$alkyl; alkyl or carboxy-alkyl.

The specified radicals and groups may be substituted. The following are particularly preferred substituents: carboxyl, carbonamide-, acetylamino-, sulphonamino-, ureido- and ester groups. The mercapto group ($-SH$) is a particularly preferred substituent for the radical $R^1$.

In a particularly preferred embodiment, $R^1$ represents the group $-CH_2-CHR^7-SH$, in which $R^7$ represents H, $CH_3$ or $C_2H_5$.

The alkyl radicals listed under $R^8$ preferably have from 1 to 5 carbon atoms; the aryl radical specified is preferably phenyl.

In another preferred embodiment, the compounds of formula (Ia) correspond to the general formula (IV):

$$R^1\!\!-\!\!(X\!-\!CHR^3\!-\!CHR^4\!-\!SH)_2 \quad (IV)$$

in which the substituents $R^1$, $R^3$ and $R^4$ have the following meanings:
- $R^1$ represents $-(-CH_2-)_q-$; $-(-CH_2-CH_2-O-)_r-C_2H_4-$; $-(-C_2H_4-S-)_s-C_2H_4-$ or $$-CH_2-\underset{\underset{CH_2}{||}}{C}-CH_2-;$$

- $R^3$ represents H or $CH_3$;
- $R^4$ represents H or $CH_3$; and/or
- $R^3$ and $R^4$ may together represent the atoms required to complete the group $-(-CH_2-)_t-$;
- q represents an integer from 2 to 8;
- r represents an integer from 1 to 100;
- s represents an integer from 1 to 3 and
- t represents 3 or 4

Particularly preferred compounds according to formula (I) are listed in the following Tables 1 and 2.

TABLE I

| No. | Compound |
|---|---|
| 1.1 | $HS-(C_2H_4S)_2-H$ |
| 1.2 | $HS-(C_2H_4S)_3-H$ |
| 1.3 | $HS-(C_2H_4S)_4-H$ |
| 1.4 | $HS-CH_2-\underset{CH_3}{CH}-S-(CH_2)_3-S-\underset{CH_3}{CH}-CH_2-SH$ |
| 1.5 | $C[CH_2-S-C_2H_4-SH]_4$ |
| 1.6 | $H-CO-N\left[\begin{array}{c}CH_2-CH-CH_2-SH\\ \vert \\ S-CH_3\end{array}\right]_2$ |
| 1.7 | $C_6H_5-S-C_2H_4-SH$ |
| 1.8 | $C_6H_5-CH_2-S-C_2H_4-SH$ |
| 1.9 | $(CH_3)_2-CH-S-\underset{CH_3}{CH}-\underset{CH_3}{\overset{\vert}{C}}-SH$ |
| 1.10 | (bis-cyclopentyl sulfide with SH groups) |
| 1.11 | $HS-\underset{CH_3}{\overset{CH_3}{CH}}-\underset{CH_3}{\overset{CH_3}{CH}}-S-\underset{CH_3}{\overset{CH_3}{CH}}-\underset{CH_3}{\overset{CH_3}{CH}}-SH$ |
| 1.12 | (bis-cyclohexyl sulfide with SH groups) |
| 1.13 | $HS-\underset{CH_3}{\overset{CH_3}{CH}}-\underset{CH_3}{\overset{CH_3}{CH}}-S-(CH_2)_3-S-\underset{CH_3}{\overset{CH_3}{CH}}-\underset{CH_3}{\overset{CH_3}{CH}}-SH$ |
| 1.14 | $HS-\underset{CH_3}{\overset{CH_3}{CH}}-\underset{CH_3}{\overset{CH_3}{CH}}-S-CH_2-\underset{CH_2}{\overset{\|}{C}}-CH_2-S-\underset{CH_3}{\overset{CH_3}{CH}}-\underset{CH_3}{\overset{CH_3}{CH}}-SH$ |
| 1.15 | $HS-\underset{CH_3}{\overset{CH_3}{CH}}-\underset{CH_3}{\overset{CH_3}{CH}}-S-\underset{CH_3}{\overset{\|}{CH}}-CH_2-S-\underset{CH_3}{\overset{CH_3}{CH}}-\underset{CH_3}{\overset{CH_3}{CH}}-SH$ |
| 1.16 | $HS-C_2H_4-S-C_2H_4-O-C_2H_4-S-C_2H_4-SH$ |
| 1.17 | $HS-C_2H_4-S-(C_2H_4-O)_2-(C_2H_4-S)_2-H$ |
| 1.18 | $HS-C_2H_4-S-(C_2H_4-O)_3-(C_2H_4S)_2-H$ |
| 1.19 | $HS-C_2H_4-S-(C_2H_4O)_7-(C_2H_4S)_2-H$ |
| 1.20 | $HS-C_2H_4-S-\underset{HS-CH_2}{\overset{\|}{CH}}-CH_2-O-(C_2H_4O)_2-CH_2-\underset{HS-CH_2}{\overset{\|}{CH}}-S-C_2H_4-SH$ |
| 1.21 | $HS-(C_2H_4-O)_2-C_2H_4-SH$ |
| 1.22 | $HS-(C_2H_4-O)_3-C_2H_4-SH$ |
| 1.23 | $HS-(C_2H_4-O)_7-C_2H_4-SH$ |
| 1.24 | $HS-C_2H_4-S-CH_2-C_6H_4-CH_2-S-C_2H_4-SH$ (meta) |

TABLE 2

| No. | Compound | |
|---|---|---|
| 2.1 | $C_2H_5-O-(CH_2-\underset{\underset{SH}{\overset{\|}{CH_2}}}{\overset{\|}{CH}}-O)_5-H$ | (Example 24) |

Compounds according to formula (III) include, in addition to $N_2H_4$, in particular phenyl hydrazine; N,N-dimethylhydrazine and N-aminomorpholine. The compounds according to formula (III) may be present in the form of salts or hydrates.

The hydrazinolysis of isothiuronium salts is a reaction known per se which is suitable for the preparation of amino guanidines. It was not known that the hydrazinolysis of isothiuronium salts was suitable for the production of slightly water-soluble and highly air- or hydrolysis-sensitive thiols in particularly high yield and purity.

It is unnecessary to provide an inert gas atmosphere. The thiol formed is apparently sufficiently protected by the hydrazine present or by the amino guanidine salt formed therefrom, from attack by atmospheric oxygen. The purity in which 2-mercaptoalkylsulphide is produced amounts to at least 97%, the disulphide content being less than 1%. In particular, the S-alkylisothiourea formed initially is continuously dissociated into thiol and amino guanidine salt.

In a particularly preferred embodiment, the hydrazine is added so that the pH value constantly remains below pH 8 during the reaction. Hydrazine is added in the form of hydrazine hydrate, optionally in diluted solution. However, hydrazine may also be added in the form of a non-volatile hydrazinium salt, the reaction thereby taking place without any danger to health. The base itself is then released by subsequently adding an equivalent quantity of alkali. It is not necessary that the quantity of hydrazine exceeds 100%, but it has been found to be advantageous in most cases to use excesses of from 5 to 15%. This does not cause any disadvantage in the process, even from the point of view of the toxicity of hydrazine, hydrazine hydrate or hydrazine compounds, because hydrazine may be easily removed from the waste liquors of the process, together with residual S-compounds by means of an oxidative after-treatment, e.g. using chlorine or hydrogen peroxide.

Since the amino guanidine salts which are inevitably produced as by-products crystallise effectively, and as they are also commercially useful compounds, their separation from the waste liquors of the process does not increase the cost of the process.

Another advantage of the process consists in the fact that it may be carried out under very mild conditions and for this reason may also be applied to compounds containing groups which are unstable to alkalis, e.g. having ester or formamide bonds.

The high yields which may be obtained are particularly important when the process is to be used for the preparation of bis- or polythiols. For this purpose, according to the invention, bis- or poly (2-hydroxy-alkyl sulphides) are converted using thiourea and a strong acid, preferably HCl, into the isothiuronium salts at approximately 100° C., and these are dissociated using the quantity of hydrazine hydrate calculated on the HCl used, at from 30° to 100° C. With tetrakis thiols, the yields amount without exception to at least 70% and with bisthiols to 90%.

The advantages of the invention are explained in the following by examples.

EXAMPLE 1

3-thiapentane-1,5-dithiol 122 g of bis-2-hydroxyethylsulphide (1 mol); 167 g of thiourea (2.2 mols) and 200 g of 37% hydrochloric acid are maintained under reflux for 3 hours in an oil bath. This is cooled to 40° C. and 110 g (2.2 mols) of hydrazine hydrate are added dropwise with stirring. The reaction mixture is then held for 30 minutes in a steam bath and 200 g of xylene are added. The reaction mixture is allowed to cool to 60° C. and the xylene phase is separated off.

Yield: 348 g (96% of the calculated quantity). By distilling the xylene phase in a water jet vacuum, 143 g (93% of the theoretical yield) of bis-mercaptodiethylsulphide are obtained.

EXAMPLE 2

1,8-dimercapto-3,6-dithiaoctane 182 g of 1,8-dihydroxy-3,6-dithiaoctane (1 mol); 167 g of thiourea (2.2 mols) and 200 g of 37% hydrochloric acid are maintained under reflux for 3 hours in an oil bath (reflux temperature 107° C.).

This is cooled to 40° C. and 110 g (2.2 mols) of hydrazine hydrate are stirred in. The reaction mixture is kept under reflux in the steam bath for one hour after adding 400 ml of xylene, cooled to 70° C. and the mercaptan phase is separated off in a separating funnel. The residue is then washed once using 100 ml of 30% acetic acid, the xylene is distilled off at normal pressure without drying and the residue is subjected to high vacuum distillation.

$Bp_1$: 200°–210° C., the product solidifies in the receiver.

Yield: 192 g (90% of the theoretical yield).

EXAMPLE 3

3,6,9-trithiaundecane-1,11-dithiol 5 ml of 10% methanolic potassium hydroxide is added to the xylene phase from Example 1 under nitrogen. Ethylene oxide is then introduced at 20° C. A total of 90 g is absorbed. The reaction mixture is maintained for 2 hours in the steam bath, the xylene is evaporated off under vacuum, 170 g of thiourea and 200 g of 37% hydrochloric acid are absorbed using 100 ml of water and the reaction mixture is maintained for 4 hours under reflux. It is then cooled to 60° C., 115 g (2.3 mols) of hydrazine hydrate are dropped in and the mixture is heated to 90° C. in the steam bath. After adding 500 ml of chlorobenzene, the reaction mixture is maintained for 1 hour at 95° C., the chlorobenzene phase is separated off in the separating funnel under nitrogen and is concentrated under vacuum.

Yield: 224 g (82% of the theoretical yield).

EXAMPLE 4

3,6-dithia-2,7-dimethylnonane-1,9-dithiol

After adding 1 g of sodium hydroxide in 10 ml of methanol, a total of 125 g (2.15 mols) of propylene oxide are added dropwise to 108 g (1 mol) of propane-1,3-dithiol at 35° C.

The reaction mixture is left to stand overnight, 170 g of thiourea and 200 g of 37% hydrochloric acid are added thereto and the mixture is maintained for 4 hours under reflux. The solution obtained is treated with 110 g (2.2 mols) of hydrazine hydrate at 40° C. and maintained for 1 hour in the steam bath after adding 300 ml of toluene. The organic phase is separated therefrom at 60° C. under nitrogen, is concentrated under vacuum and fractioned at 2 mb.

$Bp_2$: 165°–170° C.

Yield: 230 g (90% of the theoretical yield).

EXAMPLE 5 tetrakis (4-mercapto-2-thiabutyl) methane $(C_{13}H_{28}S_8)$ 75.2 g (0.2 mol) of tetrakis-(4-hydroxy-2-thiobutyl) methane is prepared from pentaerythritoltetrachloride with the 4-fold molar quantity of thioglycol in the presence of potassium hydroxide in 2-methoxy ethanol and 90 g (1.18 mols=50% excess) of thiourea and 130 g of 37% hydrochloric acid are dropped in at 90° C. This is maintained for 5 hours under reflux, cooled to 40° C. and 65 g of hydrazine hydrate and 100 ml of water are added. The reaction mixture is maintained for 2 hours under nitrogen in the steam bath, cooled to 60° C., extracted using 300 ml of chlorobenzene, the chlorobenzene phase is dried overnight using 20 g of sodium chloride concentrated under vacuum and redried at 40° C. and 2 mb.

Yield: 65 g (74% of the theoretical yield) of yellowish viscous oil.

EXAMPLE 6

Bis-(2-methyl mercapto-3-mercaptopropyl formamide)

$C_9H_{19}NS_4$

A solution of 1 mol of methane sulphenyl chloride, freshly prepared by chlorinating 0.5 mols of dimethyldisulphide with 36 g of chlorine at −25° C. in 200 ml of dichloromethane is added by dropping into the solution of 62.5 g (0.5 mol) of diallyl formamide in 300 ml of dichloromethane at −40° C. The reaction mixture is heated to room temperature and the dichloromethane is distilled off in the steam bath. This is absorbed using 300 ml of methanol, 80 g of thiourea is added and is maintained under reflux for 4 hours with stirring. While adding 300 ml of water, the methanol is then distilled off until the temperature in the reaction flask rises to 90° C. The mixture is cooled to room temperature, 53 g of hydrazine hydrate (100% calculated on thiourea) and 50 ml of water are added thereto and maintained for 1 hour in the steam bath. The mercaptan phase separated as a heavy oil is absorbed using 400 ml of toluene and the toluene phase is concentrated under vacuum after drying using 30 g of NaCl and dried at 60° C. and less than 5 torr.

Yield: 111 g (78% of the theoretical yield). The product is completely soluble in ethanol.

EXAMPLE 7

Phenylthioethanethiol 77 g of 2-phenylthioethanol, (0.5 mol, prepared from thiophenol and ethylene oxide in the presence of some potassium hydroxide) are maintained for 4 hours under reflux with 40 g of thiourea and 50 g of 37% hydrochloric acid. At 40° C., the reaction mixture is stirred with 50 g of 50% hydrazine hydrate solution for 30 minutes. 100 ml of toluene are added, this is maintained for 30 minutes in the steam bath, the toluene phase is separated off and compressed under vacuum.

Yield: 80 g (94% of the theoretical yield). By fractionation under high vacuum, in addition to 3 g of residue, the pure substance is obtained having a $Bp_1$ of from 115° to 120° C.

Yield: 75 g (88% of the theoretical yield).

EXAMPLE 8

4-phenyl-3-thiabutane-1-thiol 84 g (0.5 mol) of 2-benzylthioethanol, 40 g of thiourea (0.55 mol) and 55 g of 37% hydrochloric acid are maintained under reflux for 4 hours. After further treatment as described for Example 9, yield: 80 g (87% of the theoretical yield).

In comparison thereto, a yield of only 54% of the theoretical yield is obtained when dissociating the isothiuronium salt using 100 ml of 40% caustic soda solution and extracting using toluene and fractionating under high vacuum. Processing is hindered by the extremely slow phase separation, the high vacuum distillation produces approximately 30 g of a viscous residue which only becomes odourless using bleaching lye when left to stand for several days. Benzyl mercaptan is produced as a dissociation product in the higher boiling fractions.

EXAMPLE 9

1-amino-3,6-dithiaoctane 1060 g (10 mols) of 2-hydroxy diethylsulphide, 1150 g of 37% hydrochloric acid and 800 g of thiourea are maintained for 3 hours under reflux in an 8 liter three-neck flask. The reaction mixture is cooled to 50° C., covered with a layer of 1000 ml of xylene and a total of 570 g of hydrazine hydrate (11.4 mols) are added thereto during 10 minutes. The mixture is heated for another hour to 90° C., cooled to 70° C. and the aqueous phase is decanted. While cooling, 900 g of amino guanidine hydrochloride are separated off. The xylene phase is then washed once using 300 ml of 10% acetic acid and cooled to 40° C. At from 40° to 50° C., solutions of 1100 g (9.5 mols) of 2-chloroethyl amine hydrochloride in 1000 ml of water and 800 g (10 mols) of sodium hydroxide in 500 ml of water are added. The xylene phase is then heated and maintained for 4 hours at 90° C., then left to cool to 60° C. and the aqueous phase is removed by suction. Drying is carried out using sodium chloride, the xylene is distilled off under vacuum and the raw 1-amino-3,6-dithiaoctane is fractionated under vacuum at 40 ml (Bp 110° C.).

Yield: 1420 g (86% of the theoretical yield).

EXAMPLE 10 bis-(2-mercaptocyclopentyl)-sulphide 51.5 g (0.5 mol) of freshly distilled sulphur dichloride in 100 ml of dichloromethane are added dropwise to a solution of 68 g of cyclopentene (1 mol) in 200 ml of dichloromethane at −40° C. The dichloromethane is distilled off, absorption is carried out using 400 ml of methanol and 90 g of thiourea and the mixture is maintained for six hours in the steam bath. The methanol is evaporated off and 60 g of hydrazine hydrate (1.2 mols) in 200 ml of water are added. The reaction mixture is maintained for 1 hour in the steam bath, the oil phase is absorbed in 200 ml of toluene, the residue is washed using 20% acetic acid and the solvent is removed under vacuum and distilled.

Yield: 100 g (85% of the theoretical yield).
$Bp_1$: 170°–180° C.

EXAMPLE 11 bis-(2-mercapto-1-methylpropyl) sulphide 85 g of trans-2,3-butylene oxide are added dropwise under reflux, to a solution of 111 g (0.5 mols) of sodium sulphide-nona hydrate in 100 ml of ethanol. The reaction mixture is maintained for a further 3 hours under reflux, 60 g of glacial acetic acid are added and the mixture is evaporated. Absorption is carried out using 90 g of thiourea and 200 g of 37% hydrochloric acid, the mixture is maintained for 4 hours under reflux and evaporated under vacuum. Absorption is carried out in 300 ml of water, 60 g of hydrazine hydrate are dropped in at 40° C., maintained for 1 hour in the steam bath and the oil phase is absorbed with 200 ml of toluene. The toluene phase is washed using 100 ml of 10% acetic acid, concentrated and fractionated under high vacuum.

Yield: 80 g (76%)
$Bp_{3mb}$: 125°–140° C.

EXAMPLE 12 bis-(2-mercaptocyclohexyl)-sulphide

Preparation according to Example 10 from $Na_2S$ in cyclohexene oxide.

Yield: 85%
$Bp_2$: 180°–200° C.

EXAMPLE 13

2,10-dimercapto-3,9-dimethyl-4,8-dithiaundecane 2,10-Dioxy-3,9-dimethyl-4,8-dithia-undecane is prepared from 0.5 mol of propane-1,3-dithiol and 1.1 mol of trans-2,3-butylene oxide in the presence of 5 g of potassium hydroxide and is reacted further as described in Example 11.

Yield: 109 g (77%)
$Bp_3$: 178°–184° C.

EXAMPLE 14

2,10-Dimercapto-3,9, dimethyl-6-methylene-4,8-dithiaundecane

The preparation is carried out according to the process described in Example 11, starting from 3-mercapto-2-mercaptomethylpropene and transbutylene oxide via the diol.

Yield: 74%
$Bp_2$: 185°–200° C.

EXAMPLE 15

2,9-dimercapto-3,5,8-trimethyl-4,7-dithia-decane

The method is carried out according to the process described in Example 11 from propane-1,2-dithiol and trans-2,3-butylene oxide via the 3,5,8-trimethyl-4,7-dithiodecane-2,9-diol.

Yield: 81%
$Bp_{3mb}$: 190°–195° C.

EXAMPLE 16

1,11-dimercapto-3,9-dithia-6-oxa-undecane 1,11-dichloro-3,9-ditha-6-oxaundecane is prepared from 3,6-dithia-6-oxaundecane-1,11-diol using thionyl chloride in dichloromethane at 0° C. in the presence of 5 mol % of dimethyl formamide and is reacted with 2.3 mols of thiourea/mol for 6 hours in methanol. The reaction mixture is compressed, absorbed using water and 2.4 mols of hydrazine hydrate/mol, maintained for 1 hour in the steam bath, the oil phase is separated off by adding toluene and distilled under high vacuum.

Yield: 66%
Bp$_{5mb}$: 190°–210° C.
S(calculated): 49.6% S(found): 49.7%.

EXAMPLE 17

1,14-dimercapto-3,12-dithia-6,9-dioxatetradecane

The process is carried out as described in Example 16, starting from 2-mercapto ethanol and 1,2-bis (2-chloroethoxy)ethane via 3,12-dithia-6,9-dioxa tetra decane-1,14-diol.

Undistillable oil:
Yield 79%
S(calculated): 42.4% S(found): 41.9%.

EXAMPLE 18

1,17-dimercapto-3,15-dithia-6,9-trioxa hepta decane

The process is carried out as described in Example 16, starting from 2-mercapto ethanol and 1,11-dichloro-3,6,9-trioxa undecane.

Undistillable oil:
Yield 68%.
S(calculated): 40% S(found): 39.6%.

In a comparative Example, the 1,17-diisothiuronio-3,15-dithia-6,9,12-trioxa hepta decanedichloride, obtained as the intermediate product, is dissociated in water with a 2.5 molar quantity of potassium hydroxide. An emulsion is formed which is not broken by stirring with toluene for several hours at 60° C. After being left to stand overnight, the pH is set to pH 8 using acetic acid.

A brown smear is obtained from the toluene phase as the evaporation residue.

S(calculated): 40% S(found) 35%.
N(calculated): 0% N(found) 2.4%.

EXAMPLE 19

1,29-dimercapto-3,27-dithia-6,9,12,15,18,21,24,27-hepta oxa-nonaikosane

The method is carried out according to the process described in Example 16, starting from 2-mercapto ethanol and octa ethylene glycol dichloride via the crude 3,27-dithia-6,9,12,15,18,21,24,27-hepta oxa-nonaikosane-1,29-diol.

Yield: 70% of brown undistillable wax.
S(calculated): 24.5% S(found): 24.7%.

EXAMPLE 20

1,17-dimercapto-4,14-dimercapto methyl-3,15-dithia-6,9,12,-trioxa hepta decane 16.5 g of epichlorohydrine (0.2 mol) are added dropwise to 10.6 g (0.1 mol) of diglycol, after adding 2 ml of BF$_3$-etherate. The mixture is maintained for 2 hours in the steam bath, 200 ml of ethanol and 15.7 g (0.2 mol) of 2-mercapto ethanol are added thereto and Na-methylate in methanol is added dropwise until the mixture remains alkaline for 1 hour at boiling temperature. Neutralisation is carried out using CO$_2$, the salts being removed by suction. After concentration under vacuum, the residue is digested using 200 ml of butanol, the salts are again removed by suction and the residue concentrated under vacuum. Yield: 30 g of crude water-soluble 1,5,14,19-tetrahydroxy-3,17-dithia-7,10,13-trioxa-nonadecane.

The crude product is kept for 4 hours at 108° C. with 38 g (0.5 mol) of thiourea and 50 g of 37% hydrochloric acid, is allowed to cool and 30 g of hydrazine hydrate are stirred in. The mixture is maintained for 1 hour in the steam bath, the thiol phase is separated off using 100 ml of toluene, washed with 50 ml of 10% acetic acid and concentrated under vacuum.

Yield: 28 g of brownish viscous oil.
S(calculated): 34.2% S(found): 34.6%.

EXAMPLE 21

1,8-dimercapto-3,6-dioxa octane 187 g (1 mol) of ethylene glycol-bis(2-chloroethyl)-ether and 182 g (2.4 mols) of thiourea in 1000 ml of water are maintained for 4 hours under reflux. The clear solution is cooled to 20° C. and 120 g of hydrazine hydrate are added. After adding 400 ml of toluene, the mixture is heated for 1 hour in the steam bath. The toluene phase is separated off, concentrated under reduced pressure and distilled under vacuum.

Bp$_2$: 105°–115° C.
Yield: 153 g (84%).

According to the process described in Org. Syntheses 30, 35 (1950), in the form described by Dann and Chiesa, J. Org. Chem. 26, 1994 (1961), the yield amounts to from only 50 to 60% of the theoretical.

EXAMPLE 22

1,11-dimercapto-3,6,9-trioxaundecane

The process is carried out as in Example 21, except that 231 g (1 mol) of 1,11-dichloro-3,6,9-trioxaundecane with 245 g of imidazolidine-2-thiol (2.4 mols) are maintained for 8 hours under reflux in 1000 ml of water. Further processing is as described in Example 21.

Bp$_1$: 135°–150° C.
Yield: 178 g (79% of the theoretical yield).
S(calculated): 28.3% S(found): 28%.

EXAMPLE 23

(compound 1.23)

Bisthiol from polyglycol

The process is carried out as in Example 22, but with the difference that as the starting material, 100 g of a dichloride from a commercial polyethylene glycol (molecular weight 370) and 60 g of thiourea are used. 80 g of a water-insoluble oil are obtained.

S(calculated): 16% S(found) 15%.

EXAMPLE 24

(compound 2.1)

40 g of thiourea (~0.5 mol) are added to 52 g (0.1 mol) of an adduct of ethanol and the 5-fold molar quantity of epichlorohydrin, prepared by adding epichlorohydrin dropwise in the presence of 2 mol % of BF$_3$-ether and heating for 4 hours in the steam bath, and maintaining the reaction mixture for 8 hours in the steam bath with 100 ml of ethanol and 20 ml of water. Digestion is then carried out with 30 ml of hydrazine hydrate for 1 hour in the steam bath, separating using 200 ml of toluene at elevated temperature, washing the toluene phase with 100 ml of water, drying with sodium chloride and concentrating under vacuum.

Yield: 45 g.

EXAMPLE 25

Example 1 is repeated, but with the difference that the xylene phase is returned to the reaction vessel after separating the amino guanidine-HCl phase and is maintained with stirring at 90° C. for 1 hour with the solution of 200 g of chloroacetic acid and 88 g of sodium hydroxide in 1000 ml of water. The aqueous phase is then separated and acidified using dilute HCl at from +10° to 20° C. The precipitated crystals are removed with suction, washed with water and recrystallised.

Yield: 232 g (90% of the theoretical yield).
2,5,8-trithianonane-1,9-dicarboxylic acid.
Bp: 110° C.

Even in the stage of the crude product, the substance has only a slight mercaptan smell and it is odourless after a single crystallisation step from water or methanol.

Thus, the compounds prepared according to the invention may be further processed, optionally without a purification step.

We claim:

1. A process for the preparation of a compound of the following structural formula

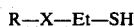     (I)

by treating a compound of the following structural formula

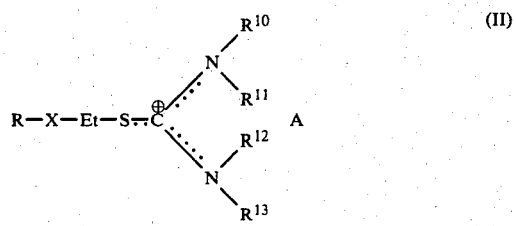     (II)

with a compound of the following structural formula

     (III)

in which
R represents an organic radical comprising at least one alkyl, aralkyl or aryl group which may be substituted and which may be interrupted by S- and/or O-atoms, X represents an oxygen atom or a sulphur atom, Et represents an ethylene group which may be substituted and which may form part of a 5- or 6-membered ring system, $R^{10}$ to $R^{13}$ which may be the same or different, represent H; an alkyl group having from 1-6 C-atoms which may be substituted or an aryl radical which may be substituted and/or at least one pair of the substituents $R^{10}$ to $R^{13}$ may represent the atoms required to complete a heterocyclic 5- or 6-membered ring, $R^{20}$ to $R^{22}$ which may be the same or different, represent hydrogen, an alkyl group having from 1-5 C-atoms or aryl radical which may be substituted or $R^{20}$ together with $R^{21}$ represent the atoms required to complete a ring, A represents an anion which may be multivalent.

2. A process according to claim 1, wherein the the reaction takes place between 0° and 120° C. at pH 6 to 12.

3. A process for the preparation of a compound of a structure according to formula Ia or Ib:

     (Ia)

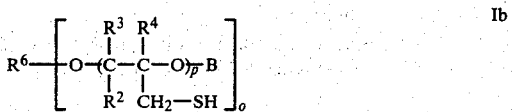     Ib in which:
$R^1$ represents an aliphatic radical having from 2 to 20 carbon atoms, which may be substituted by aryl or interrupted by phenylene, or by O or S atoms, or an alicyclic radical, having from 5 to 7 carbon atoms, or phenyl, chlorophenyl, o-carboxy phenyl, benzyl,
and said $R^1$ radical may be substituted with a mercapto group;

$R^2$, $R^3$, $R^4$ and $R^5$ which may be the same or different represent hydrogen; an alkyl group, having from 1 to 6 carbon atoms which may be substituted; phenyl, and/or
at least one pair from the group $R^2$ to $R^5$ represents the atoms required to complete a 5- or 6-membered ring;

X represents an oxygen atom or a sulphur atom;

$R^6$ represents H or:
an aliphatic radical having 2 to 10 aliphatically bound carbon atoms, which may be substituted by aryl or cycloalkyl or interrupted by arylene or a radical derived from a polyalkylene oxide having from 4 to 20 carbon atoms interrupted by ether groups,
a phenyl or phenylene groups, which may be interrupted by alkylene groups,
an alicyclic radical, having from 5 to 7 carbon atoms, or benzyl or phenethyl;
the $R^6$ group may be interrupted by at least one oxygen and/or sulphur atom, m represents an integer from 1 to 100;
n represents an integer from 1 to 4;
o represents an integer from 1 to 3;
p represents an integer of from 2 to 20;
B represents H or —CO—$R^8$; and
$R^8$ represents —NH-alkyl; —NH-aryl; —O-alkyl; alkyl or carboxy-alkyl,
and said $R^1$, $R^2$, $R^3$, $R^4$, $R^5$, $R^6$ and $R^8$ radicals and groups may be substituted with carboxyl, carbonamide-, acetylamino- sulphonamino-, ureido- and ester groups,
by reacting the S-alkyl- isothiuronium salt of compound Ia or Ib with a hydrazine of the following structural formula

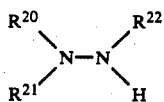

in which
R$^{20}$ to R$^{22}$ may be the same or different, represent hydrogen,
an alkyl group having from 1–5 C-atoms or aryl radical which may be substituted or
R$^{20}$ together with R$^{21}$ represent the atoms required to complete a ring.

4. A process according to claim 3, wherein
R$^1$ represents alkyl having from 2 to 20 carbon atoms; phenyl or benzyl,
R$^2$ to R$^5$ represent H; alkyl having from 1 to 6 carbon atoms; phenyl and/or at least one pair from the substitutents R$^2$ to R$^5$ represent the atoms required to complete a cyclopentyl or cyclohexyl ring,
x represents oxygen or sulphur,
R$^6$ represents alkyl having 2 to 10 carbon atoms; phenyl, benzyl or phenethyl;
m represents an integer from 1 to 100;
n represents an integer from 1 to 4;
o represents an integer from 1 to 3;
p represents an integer from 2 to 20 and
B represents hydrogen.

5. A process according to claim 4, wherein
R$^1$ represents —CH$_2$—CHR$^7$—SH, and
R$^7$ represents H, CH$_3$ or C$_2$H$_5$.

6. A process as claimed in claim 3 wherein the hydrazine is selected from the group consisting of phenyl hydrazine; N,N-dimethylhydrazine, N-aminomorpholine and their salts and hydrates.

* * * * *